US009230532B1

(12) United States Patent
Lu et al.

(10) Patent No.: US 9,230,532 B1
(45) Date of Patent: Jan. 5, 2016

(54) POWER MANAGEMENT OF ADAPTIVE NOISE CANCELLATION (ANC) IN A PERSONAL AUDIO DEVICE

(71) Applicant: Cirrus Logic, Inc., Austin, TX (US)

(72) Inventors: Yang Lu, Austin, TX (US); Dayong Zhou, Austin, TX (US); Jon D. Hendrix, Wimberly, TX (US); Jeffrey Alderson, Austin, TX (US)

(73) Assignee: Cirrus, Logic Inc., Austin, TX (US)

( * ) Notice: Subject to any disclaimer, the term of this patent is extended or adjusted under 35 U.S.C. 154(b) by 280 days.

(21) Appl. No.: 13/794,931

(22) Filed: Mar. 12, 2013

Related U.S. Application Data

(60) Provisional application No. 61/701,187, filed on Sep. 14, 2012.

(51) Int. Cl.
*A61F 11/06* (2006.01)
*G10K 11/16* (2006.01)
(Continued)

(52) U.S. Cl.
CPC ............ *G10K 11/16* (2013.01); *G10K 11/1784* (2013.01)

(58) Field of Classification Search
CPC ................ G10K 11/1784; G10K 2210/30232; G10K 2210/3045; G10K 11/178; G10K 11/1788; G10K 2210/1081; G10K 2210/3023; G10K 11/16; H04R 1/1083
USPC .......................... 381/71.2, 71.1, 71.11, 71.12
See application file for complete search history.

(56) References Cited

U.S. PATENT DOCUMENTS

| | | | |
|---|---|---|---|
| 5,251,263 | A | 10/1993 | Andrea et al. |
| 5,278,913 | A | 1/1994 | Delfosse et al. |
| 5,321,759 | A | 6/1994 | Yuan |

(Continued)

FOREIGN PATENT DOCUMENTS

| | | | |
|---|---|---|---|
| DE | 102011013343 | A1 | 9/2012 |
| EP | 1880699 | A2 | 1/2008 |

(Continued)

OTHER PUBLICATIONS

Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.

(Continued)

*Primary Examiner* — Vivian Chin
*Assistant Examiner* — Douglas Suthers
(74) *Attorney, Agent, or Firm* — Mitch Harris, Atty at Law, LLC; Andrew M. Harris

(57) ABSTRACT

A personal audio device, such as a wireless telephone, includes an adaptive noise canceling (ANC) circuit that adaptively generates an anti-noise signal from an output of a microphone that measures ambient audio. The anti-noise signal is combined with source audio to provide an output for a speaker. The anti-noise signal causes cancellation of ambient audio sounds that appear at the microphone. A processing circuit estimates a level of background noise from the microphone output and sets a power conservation mode of the personal audio device in response to detecting that the background noise level is lower than a predetermined threshold.

27 Claims, 6 Drawing Sheets

(51) Int. Cl.
*H03B 29/00* (2006.01)
*G10K 11/178* (2006.01)

(56) References Cited

U.S. PATENT DOCUMENTS 5,337,365 A 8/1994 Hamabe et al.
5,359,662 A 10/1994 Yuan et al.
5,410,605 A 4/1995 Sawada et al.
5,425,105 A 6/1995 Lo et al.
5,445,517 A 8/1995 Kondou et al.
5,465,413 A 11/1995 Enge et al.
5,548,681 A 8/1996 Gleaves et al.
5,586,190 A 12/1996 Trantow et al.
5,640,450 A 6/1997 Watanabe
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,946,391 A 8/1999 Dragwidge et al.
5,991,418 A 11/1999 Kuo
6,041,126 A 3/2000 Terai et al.
6,118,878 A 9/2000 Jones
6,219,427 B1 4/2001 Kates et al.
6,278,786 B1 8/2001 McIntosh
6,282,176 B1 8/2001 Hemkumar
6,418,228 B1 7/2002 Terai et al.
6,434,246 B1 8/2002 Kates et al.
6,434,247 B1 8/2002 Kates et al.
6,522,746 B1 2/2003 Marchok et al.
6,683,960 B1 1/2004 Fujii et al.
6,766,292 B1 7/2004 Chandran
6,768,795 B2 7/2004 Feltstrom et al.
6,850,617 B1 2/2005 Weigand
6,940,982 B1 9/2005 Watkins
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,680,456 B2 3/2010 Muhammad et al.
7,742,790 B2 6/2010 Konchitsky et al.
7,817,808 B2 10/2010 Konchitsky et al.
8,019,050 B2 9/2011 Mactavish et al.
8,249,262 B2 8/2012 Chua et al.
8,290,537 B2 10/2012 Lee et al.
8,325,934 B2 12/2012 Kuo
8,379,884 B2 2/2013 Horibe et al.
8,401,200 B2 3/2013 Tiscareno et al.
8,442,251 B2 5/2013 Jensen et al.
8,804,974 B1 8/2014 Melanson
8,908,877 B2 12/2014 Abdollahzadeh Milani et al.
2001/0053228 A1 12/2001 Jones
2002/0003887 A1 1/2002 Zhang et al.
2003/0063759 A1 4/2003 Brennan et al.
2003/0072439 A1 4/2003 Gupta
2003/0185403 A1 10/2003 Sibbald
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0035593 A1 2/2006 Leeds
2006/0055910 A1 3/2006 Lee
2006/0069556 A1 3/2006 Nadjar et al.
2006/0153400 A1 7/2006 Fujita et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0177532 A1 7/2008 Greiss et al.
2008/0181422 A1 7/2008 Christoph
2008/0226098 A1 9/2008 Haulick et al.
2008/0240413 A1 10/2008 Mohammad et al.
2008/0240455 A1 10/2008 Inoue et al.
2008/0240457 A1 10/2008 Inoue et al.
2009/0012783 A1 1/2009 Klein
2009/0034748 A1 2/2009 Sibbald
2009/0041260 A1 2/2009 Jorgensen et al.
2009/0046867 A1 2/2009 Clemow
2009/0060222 A1 3/2009 Jeong et al.
2009/0080670 A1 3/2009 Solbeck et al.
2009/0086990 A1 4/2009 Christoph
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.
2009/0311979 A1 12/2009 Husted et al.
2010/0014683 A1 1/2010 Maeda et al.
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0098265 A1 4/2010 Pan et al.
2010/0124335 A1 5/2010 Shridhar et al.
2010/0124336 A1 5/2010 Shridhar et al.
2010/0124337 A1 5/2010 Wertz et al.
2010/0131269 A1 5/2010 Park et al.
2010/0142715 A1 6/2010 Goldstein et al.
2010/0150367 A1 6/2010 Mizuno
2010/0158330 A1 6/2010 Guissin et al.
2010/0166203 A1 7/2010 Peissig et al.
2010/0195838 A1 8/2010 Bright
2010/0195844 A1 8/2010 Christoph et al.
2010/0207317 A1 8/2010 Iwami et al.
2010/0246855 A1 9/2010 Chen
2010/0266137 A1* 10/2010 Sibbald et al. ............... 381/71.6
2010/0272276 A1 10/2010 Carreras et al.
2010/0272283 A1 10/2010 Carreras et al.
2010/0274564 A1 10/2010 Bakalos et al.
2010/0284546 A1 11/2010 DeBrunner et al.
2010/0291891 A1 11/2010 Ridgers et al.
2010/0296666 A1 11/2010 Lin
2010/0296668 A1 11/2010 Lee et al.
2010/0310086 A1 12/2010 Magrath et al.
2010/0322430 A1 12/2010 Isberg
2011/0007907 A1 1/2011 Park et al.
2011/0106533 A1 5/2011 Yu
2011/0129098 A1 6/2011 Delano et al.
2011/0130176 A1 6/2011 Magrath et al.
2011/0142247 A1 6/2011 Fellers et al.
2011/0144984 A1 6/2011 Konchitsky
2011/0158419 A1 6/2011 Theverapperuma et al.
2011/0206214 A1 8/2011 Christoph et al.
2011/0222698 A1 9/2011 Asao et al.
2011/0249826 A1 10/2011 Van Leest
2011/0288860 A1 11/2011 Schevciw et al.
2011/0293103 A1 12/2011 Park et al.
2011/0299695 A1 12/2011 Nicholson
2011/0305347 A1 12/2011 Wurm

(56) References Cited

U.S. PATENT DOCUMENTS

| | | | |
|---|---|---|---|
| 2011/0317848 | A1 | 12/2011 | Ivanov et al. |
| 2012/0135787 | A1 | 5/2012 | Kusunoki et al. |
| 2012/0140917 | A1 | 6/2012 | Nicholson et al. |
| 2012/0140942 | A1 | 6/2012 | Loeda |
| 2012/0140943 | A1 | 6/2012 | Hendrix et al. |
| 2012/0148062 | A1 | 6/2012 | Scarlett et al. |
| 2012/0155666 | A1 | 6/2012 | Nair |
| 2012/0170766 | A1 | 7/2012 | Alves et al. |
| 2012/0215519 | A1 | 8/2012 | Park et al. |
| 2012/0250873 | A1 | 10/2012 | Bakalos et al. |
| 2012/0259626 | A1 | 10/2012 | Li et al. |
| 2012/0263317 | A1 | 10/2012 | Shin et al. |
| 2012/0300958 | A1 | 11/2012 | Klemmensen |
| 2012/0300960 | A1 | 11/2012 | Mackay et al. |
| 2012/0308021 | A1 | 12/2012 | Kwatra et al. |
| 2012/0308024 | A1 | 12/2012 | Alderson et al. |
| 2012/0308025 | A1 | 12/2012 | Hendrix et al. |
| 2012/0308026 | A1 | 12/2012 | Kamath et al. |
| 2012/0308027 | A1 | 12/2012 | Kwatra |
| 2012/0308028 | A1 | 12/2012 | Kwatra et al. |
| 2012/0310640 | A1 | 12/2012 | Kwatra et al. |
| 2013/0010982 | A1 | 1/2013 | Elko et al. |
| 2013/0083939 | A1 | 4/2013 | Fellers et al. |
| 2013/0243198 | A1 | 9/2013 | Van Rumpt |
| 2013/0243225 | A1 | 9/2013 | Yokota |
| 2013/0272539 | A1 | 10/2013 | Kim et al. |
| 2013/0287218 | A1 | 10/2013 | Alderson et al. |
| 2013/0287219 | A1 | 10/2013 | Hendrix et al. |
| 2013/0301842 | A1 | 11/2013 | Hendrix et al. |
| 2013/0301846 | A1 | 11/2013 | Alderson et al. |
| 2013/0301847 | A1 | 11/2013 | Alderson et al. |
| 2013/0301848 | A1 | 11/2013 | Zhou et al. |
| 2013/0301849 | A1 | 11/2013 | Alderson et al. |
| 2013/0343556 | A1 | 12/2013 | Bright |
| 2013/0343571 | A1 | 12/2013 | Rayala et al. |
| 2014/0044275 | A1 | 2/2014 | Goldstein et al. |
| 2014/0050332 | A1 | 2/2014 | Nielsen et al. |
| 2014/0072134 | A1 | 3/2014 | Po et al. |
| 2014/0086425 | A1 | 3/2014 | Jensen et al. |
| 2014/0177851 | A1 | 6/2014 | Kitazawa et al. |
| 2014/0211953 | A1 | 7/2014 | Alderson et al. |
| 2014/0270222 | A1 | 9/2014 | Hendrix et al. |
| 2014/0270223 | A1 | 9/2014 | Li et al. |
| 2014/0270224 | A1 | 9/2014 | Zhou et al. |
| 2015/0092953 | A1 | 4/2015 | Abdollahzadeh Milani et al. |

FOREIGN PATENT DOCUMENTS

| | | | |
|---|---|---|---|
| EP | 1947642 | A1 | 7/2008 |
| EP | 2133866 | A1 | 12/2009 |
| EP | 2216774 | A1 | 8/2010 |
| EP | 2237573 | A1 | 10/2010 |
| EP | 2395500 | A1 | 12/2011 |
| EP | 2395501 | A1 | 12/2011 |
| GB | 2401744 | A | 11/2004 |
| GB | 2455821 | A | 6/2009 |
| GB | 2455824 | A | 6/2009 |
| GB | 2455828 | A | 6/2009 |
| GB | 2484722 | A | 4/2012 |
| JP | H06-186985 | A | 7/1994 |
| WO | WO 9911045 | | 3/1999 |
| WO | WO 03/015074 | A1 | 2/2003 |
| WO | WO 2003015275 | A1 | 2/2003 |
| WO | WO 2004009007 | A1 | 1/2004 |
| WO | WO 2004017303 | A1 | 2/2004 |
| WO | WO 2007007916 | A1 | 1/2007 |
| WO | WO 2007113487 | A1 | 11/2007 |
| WO | WO 2010117714 | A1 | 10/2010 |
| WO | WO 2012134874 | A1 | 10/2012 |
| WO | WO 2015038255 | A1 | 3/2015 |

OTHER PUBLICATIONS

Jin, et al. "A simultaneous equation method-based online secondary path modeling algorithm for active noise control", Journal of Sound and Vibration, Apr. 25, 2007, pp. 455-474, vol. 303, No. 3-5, London, GB.

Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.

Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.

Rangachari, et al., "A noise-estimation algorithm for highly non-stationary environments", Speech Communication, Feb. 2006, pp. 220-231, vol. 48, No. 2. Elsevier Science Publishers.

U.S. Appl. No. 13/968,007, filed Aug. 15, 2013, Hendrix, et al.

U.S. Appl. No. 14/029,159, filed Sep. 17, 2013, Li, et al.

U.S. Appl. No. 14/062,951, filed Oct. 25, 2013, Zhou, et al.

U.S. Appl. No. 14/197,814, filed Mar. 5, 2014, Kaller, et al.

U.S. Appl. No. 14/210,537, filed Mar. 14, 2014, Abdollahzadeh Milani, et al.

U.S. Appl. No. 14/210,589, filed Mar. 14, 2014, Abdollahzadeh Milani, et al.

Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.

Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.

Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.

Liu, et al., "Compensatory Responses to Loudness-shifted Voice Feedback During Production of Mandarin Speech", Journal of the Acoustical Society of America, Oct. 2007, pp. 2405-2412, vol. 122, No. 4.

Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.

Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.

Parkins, et al., "Narrowband and broadband active control in an enclosure using the acoustic energy density", J. Acoust. Soc. Am. Jul. 2000, pp. 192-203, vol. 108, issue 1, US.

Feng, et al.., "A broadband self-tuning active noise equaliser", Signal Processing, Oct 1, 1997, pp. 251-256, vol. 62, No. 2, Elsevier Science Publishers B.V. Amsterdam, NL.

Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.

Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.

U.S. Appl. No. 13/686,353, filed Nov. 27, 2012, Hendrix, et al.

U.S. Appl. No. 13/795,160, filed Mar. 12, 2013, Hendrix, et al.

U.S. Appl. No. 13/692,367, filed Dec. 3, 2012, Alderson, et al.

U.S. Appl. No. 13/722,119, filed Dec. 20, 2012, Hendrix, et al.

U.S. Appl. No. 13/727,718, filed Dec. 27, 2012, Alderson et al.

U.S. Appl. No. 13/784,018, filed Mar. 4, 2013, Alderson, et al.

U.S. Appl. No. 13/787,906, filed Mar. 7, 2013, Alderson, et al.

U.S. Appl. No. 13/729,141, filed Dec. 28, 2012, Zhou, et al.

U.S. Appl. No. 13/794,979, filed Mar. 12, 2013, Alderson, et al.

Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.

(56) References Cited

OTHER PUBLICATIONS

Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2102, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed, Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
U.S. Appl. No. 14/734,321, filed Jun. 9, 2015, Alderson, et al.
U.S. Appl. No. 14/578,567, filed Dec. 22, 2014, Kwatra, et al.
Widrow, B., et al., Adaptive Noise Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
U.S. Appl. No. 14/656,124, filed Mar. 12, 2015, Hendrix, et al.

* cited by examiner

POWER MANAGEMENT OF ADAPTIVE NOISE CANCELLATION (ANC) IN A PERSONAL AUDIO DEVICE

BACKGROUND OF THE INVENTION

1. Field of the Invention

The present invention relates generally to personal audio devices such as headphones that include adaptive noise cancellation (ANC), and, more specifically, to power management in an ANC system.

2. Background of the Invention

Wireless telephones, such as mobile/cellular telephones, cordless telephones, and other consumer audio devices, such as MP3 players, are in widespread use. Performance of such devices with respect to intelligibility can be improved by providing adaptive noise canceling (ANC) using a reference microphone to measure ambient acoustic events and then using signal processing to insert an anti-noise signal into the output of the device to cancel the ambient acoustic events.

Since personal devices such as those described above are generally battery-powered, power management of features within the device are needed in order to extend battery life. Further, reduction of power consumption of electronic devices is desirable in general. Therefore, it would be desirable to provide a personal audio device, including a wireless telephone, which provides noise cancellation in which the noise cancellation features are power-managed.

SUMMARY OF THE INVENTION

The above-stated objectives of providing power management of noise cancellation features in a personal audio device is accomplished in a personal audio system, a method of operation, and an integrated circuit.

The personal audio device includes an output transducer for reproducing an audio signal that includes both source audio for playback to a listener and an anti-noise signal for countering the effects of ambient audio sounds in an acoustic output of the transducer. The personal audio device also includes the integrated circuit to provide adaptive noise canceling (ANC) functionality. The method is a method of operation of the personal audio system and integrated circuit. A microphone is mounted on the device housing to provide a microphone signal indicative of the ambient audio sounds. The personal audio system further includes an ANC processing circuit for adaptively generating the anti-noise signal from the microphone signal using an adaptive filter, such that the anti-noise signal causes substantial cancellation of the ambient audio sounds. The ANC processing circuit further estimates a background noise level from the microphone signal and sets a power conservation mode of the personal audio device in response to detecting that the background noise level is lower than a predetermined threshold.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

Noise-canceling techniques and circuits that can be implemented in a personal audio device, such as a wireless telephone, are disclosed. The personal audio device includes an adaptive noise canceling (ANC) circuit that measures the ambient acoustic environment and generates a signal that is injected into the speaker (or other transducer) output to cancel ambient acoustic events. The ANC circuit also estimates the background noise level, and when the background noise level is below a threshold, the ANC circuit sets a power conservation mode of the personal audio device, conserving energy when ANC operation is not required.

Figure 1:
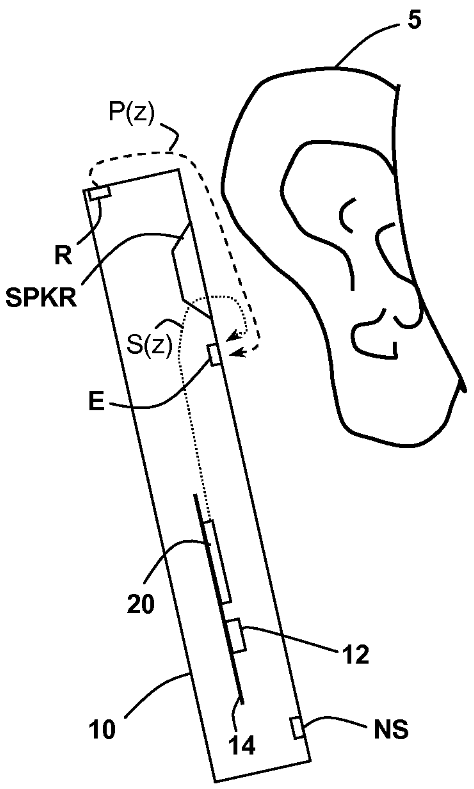
FIG. 1 is an illustration of an exemplary wireless telephone 10.

FIG. 1 shows an exemplary wireless telephone 10 in proximity to a human ear 5. Illustrated wireless telephone 10 is an example of a device in which techniques illustrated herein may be employed, but it is understood that not all of the elements or configurations embodied in illustrated wireless telephone 10, or in the circuits depicted in subsequent illustrations, are required. Wireless telephone 10 includes a transducer, such as speaker SPKR, that reproduces distant speech received by wireless telephone 10, along with other local audio events such as ringtones, stored audio program material, near-end speech, sources from web-pages or other network communications received by wireless telephone 10 and audio indications such as battery low and other system event notifications. A near-speech microphone NS is provided to capture near-end speech, which is transmitted from wireless telephone 10 to the other conversation participant(s).

Wireless telephone 10 includes adaptive noise canceling (ANC) circuits and features that inject an anti-noise signal into speaker SPKR to improve intelligibility of the distant speech and other audio reproduced by speaker SPKR. A reference microphone R is provided for measuring the ambient acoustic environment and is positioned away from the typical position of a user/talker's mouth, so that the near-end speech is minimized in the signal produced by reference microphone R. A third microphone, error microphone E, is provided in order to further improve the ANC operation by providing a measure of the ambient audio combined with the audio signal reproduced by speaker SPKR close to ear 5, when wireless telephone 10 is in close proximity to ear 5. Exemplary circuit 14 within wireless telephone 10 includes an audio CODEC integrated circuit 20 that receives the signals from reference microphone R, near speech microphone NS, and error microphone E and interfaces with other integrated circuits such as an RF integrated circuit 12 containing the wireless telephone transceiver. In other implementations, the circuits and techniques disclosed herein may be incorporated in a single integrated circuit that contains control circuits and other functionality for implementing the entirety of the personal audio device, such as an MP3 player-on-a-chip integrated circuit.

In general, the ANC techniques disclosed herein measure ambient acoustic events (as opposed to the output of speaker SPKR and/or the near-end speech) impinging on reference microphone R, and by also measuring the same ambient acoustic events impinging on error microphone E, the ANC processing circuits of illustrated wireless telephone 10 adapt an anti-noise signal generated from the output of reference microphone R to have a characteristic that minimizes the amplitude of the ambient acoustic events present at error microphone E. Since acoustic path P(z) extends from reference microphone R to error microphone E, the ANC circuits are essentially estimating acoustic path P(z) combined with removing effects of an electro-acoustic path S(z). Electro-acoustic path S(z) represents the response of the audio output circuits of CODEC IC 20 and the acoustic/electric transfer function of speaker SPKR including the coupling between speaker SPKR and error microphone E in the particular acoustic environment. Electro-acoustic path S(z) is affected by the proximity and structure of ear 5 and other physical objects and human head structures that may be in proximity to wireless telephone 10, when wireless telephone 10 is not firmly pressed to ear 5. While the illustrated wireless telephone 10 includes a two microphone ANC system with a third near speech microphone NS, other systems that do not include separate error and reference microphones can implement the above-described techniques. Alternatively, near speech microphone NS can be used to perform the function of the reference microphone R in the above-described system. Finally, in personal audio devices designed only for audio playback, near speech microphone NS will generally not be included, and the near-speech signal paths in the circuits described in further detail below can be omitted.

Figure 2:
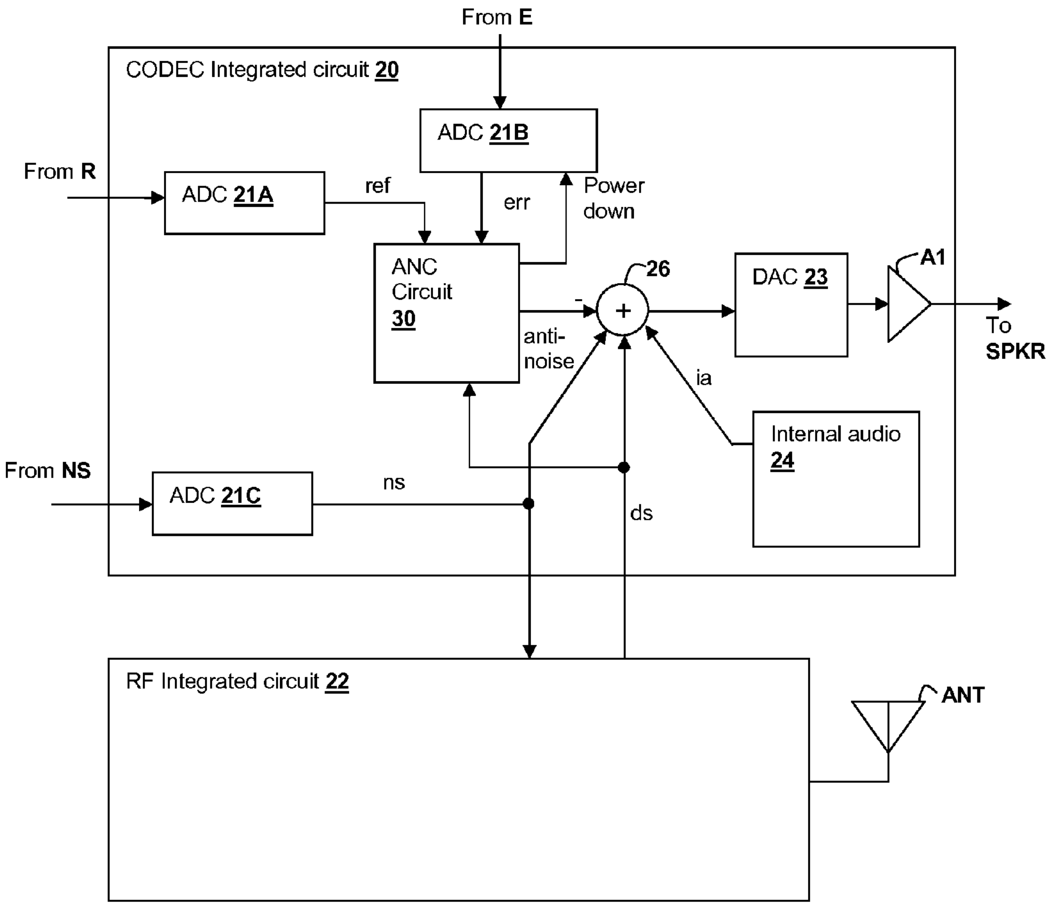
FIG. 2 is a block diagram of circuits within wireless telephone 10.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation of near speech microphone signal ns. CODEC IC 20 generates an output for driving speaker SPKR or headphones from an amplifier A1, which amplifies the output of a digital-to-analog converter (DAC) 23 that receives the output of a combiner 26. Combiner 26 combines audio signals is from internal audio sources 24, the anti-noise signal anti-noise generated by an ANC circuit 30, which by convention has the same polarity as the noise in reference microphone signal ref and is therefore subtracted by combiner 26. Additionally, combiner 26 also combines a portion of near speech signal ns so that the user of wireless telephone 10 hears their own voice in proper relation to downlink speech ds, which is received from a radio frequency (RF) integrated circuit 22. In the exemplary circuit, downlink speech ds is provided to ANC circuit 30. The downlink speech ds and internal audio is are provided to combiner 26 to provide source audio (ds+ia), so that source audio (ds+ia) may be presented to estimate acoustic path S(z) with a secondary path adaptive filter within ANC circuit 30. Near speech signal ns is also provided to RF integrated circuit 22 and is transmitted as uplink speech to the service provider via antenna ANT. ANC circuit 30 includes features to measure the ambient background noise, and determine when a low-power or power-down mode may be set for at least a portion of ANC circuit 30. Further, ANC circuit 30 provides a control signal power down that may be used to signal to other circuits within personal audio device 10 that ANC circuit 30 has determined that ANC operation is not needed. For example, control signal power down might be used to control an operational state of ADC 21B that provides error microphone signal err, during times that reference microphone signal ref indicates that the background noise level is low and ANC operation is halted.

Figure 3:
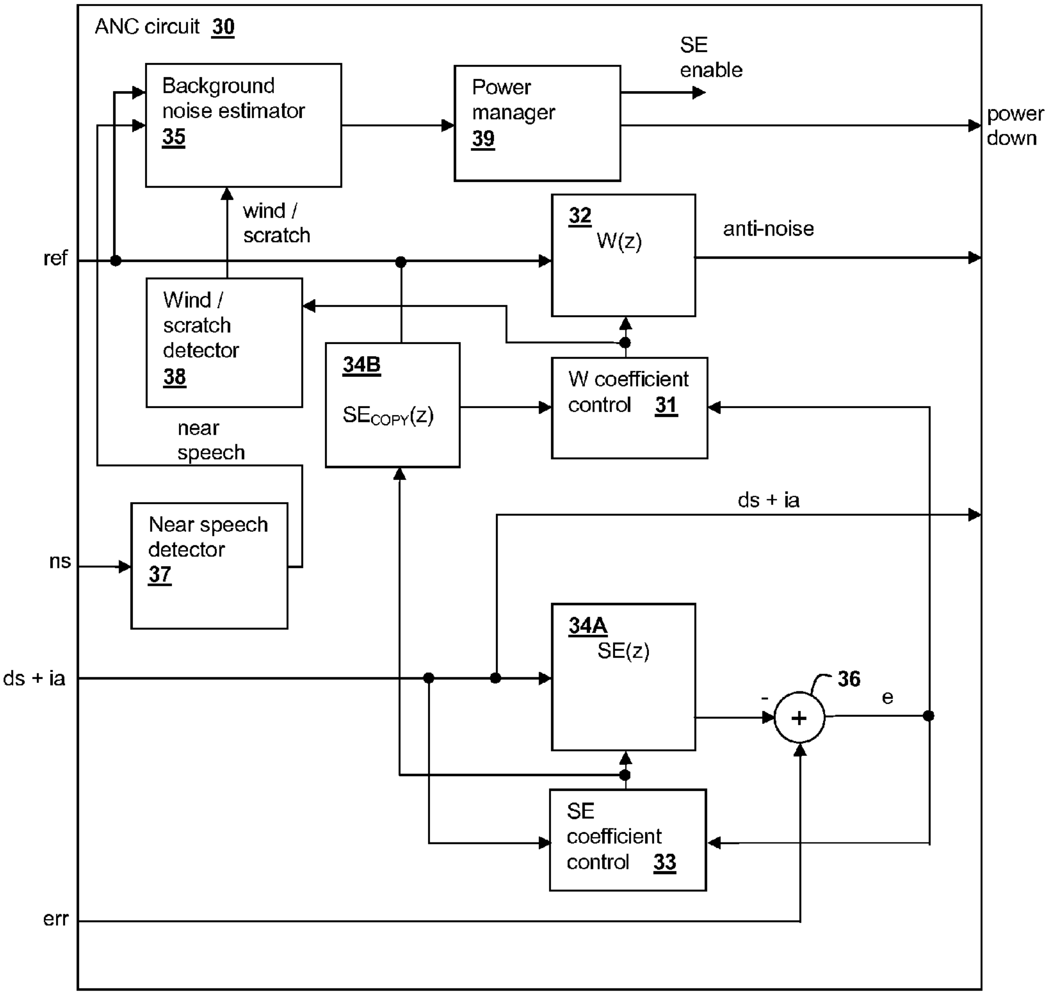
FIG. 3 is a block diagram depicting signal processing circuits and functional blocks of an exemplary circuit that can be used to implement ANC circuit 30 of CODEC integrated circuit 20 of FIG. 2.

Referring now to FIG. 3, details of ANC circuit 30 are shown. An adaptive filter 32 receives reference microphone signal ref and under ideal circumstances, adapts its transfer function W(z) to be P(z)/S(z) to generate anti-noise signal anti-noise, which is provided to an output combiner that combines the anti-noise signal with the audio to be reproduced by speaker SPKR, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err. The signals processed by W coefficient control block 31 are reference microphone signal ref shaped by a copy of an estimate of the response of path S(z) (i.e., response $SE_{COPY}(z)$) provided by a filter 34B and another signal that includes error microphone signal err. By transforming reference microphone signal ref with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z).

In addition to error microphone signal err, the other signal processed along with the output of filter 34B by W coefficient control block 31 includes an inverted amount of the source audio (ds+ia), which is processed by a filter 34A having response SE(z), of which response $SE_{COPY}(z)$ is a copy. Filter 34B is not an adaptive filter, per se, but has an adjustable response that is tuned to match the response of adaptive filter 34A, so that the response of filter 34B tracks the adapting of adaptive filter 34A. To implement the above, adaptive filter 34A has coefficients controlled by an SE coefficient control block 33. Adaptive filter 34A processes source audio (ds+ia), to provide a signal representing the expected source audio delivered to error microphone E. Adaptive filter 34A is thereby adapted to generate a signal from source audio (ds+ia), that when subtracted from error microphone signal err, forms an error signal e containing the content of error microphone signal err that is not due to source audio (ds+ia). A combiner 36 removes the filtered source audio (ds+ia) from error microphone signal err to generate error signal e. By removing an amount of source audio that has been filtered by response SE(z), adaptive filter 32 is prevented from adapting to the relatively large amount of source audio present in error microphone signal err.

Within ANC circuit 30, a background noise estimator 35 determines a value corresponding to a background noise level present in reference microphone signal ref. Alternatively other microphone signals could be used as input to background noise estimator 35, such as the outputs of near speech microphone ns or error microphone err. However, reference microphone ref will generally not be occluded by a listener's ear as will error microphone err, and will have less near speech content than near speech microphone ns, and as will be seen below, the background noise level estimate should not include near speech components. A near speech detector 37, which may be the voice activity detector (VAD) used for other purposes within wireless telephone 10, indicates to background noise estimator 35 when near speech is present. Similarly, a wind/scratch detector 38 indicates to background noise estimator 35 when wind or other mechanical noise is present at wireless telephone 10. Wind/scratch detector 38 computes the time derivative of the sum $\Sigma|W_n(z)|$ of the magnitudes of the coefficients $W_n(z)$ that shape the response of adaptive filter 32, which is an indication of the variation overall gain of the response of adaptive filter 32. Large variations in sum $\Sigma|W_n(z)|$ indicate that mechanical noise such as that produced by wind incident on reference microphone R or varying mechanical contact (e.g., scratching) on the housing of wireless telephone 10, or other conditions such as an adaptation step size that is too large and causes unstable operation has been used in the system. Wind/scratch detector 38 then compares the time derivative of sum $\Sigma|W_n(z)|$ to a threshold to determine when mechanical noise is present, and provides an indication of the presence of mechanical noise to background noise estimator 35 while the mechanical noise condition exists. While wind/scratch detector 38 provides one example of wind/scratch measurement, other alternative techniques for detecting wind and/or mechanical noise could be used to provide such an indication to background noise estimator 35. Background noise estimator 35 provides an indication to a power manager 39 of the amount of background noise present in reference microphone signal and power manager generates one or more control signals to control the power-management state of circuits within wireless telephone 10, for example control signal power down as described above. Another power-saving state can be supported, for example, by an optional control signal SE enable that causes a portion of the circuits power-managed by control signal power down to remain enabled.

Figure 4:
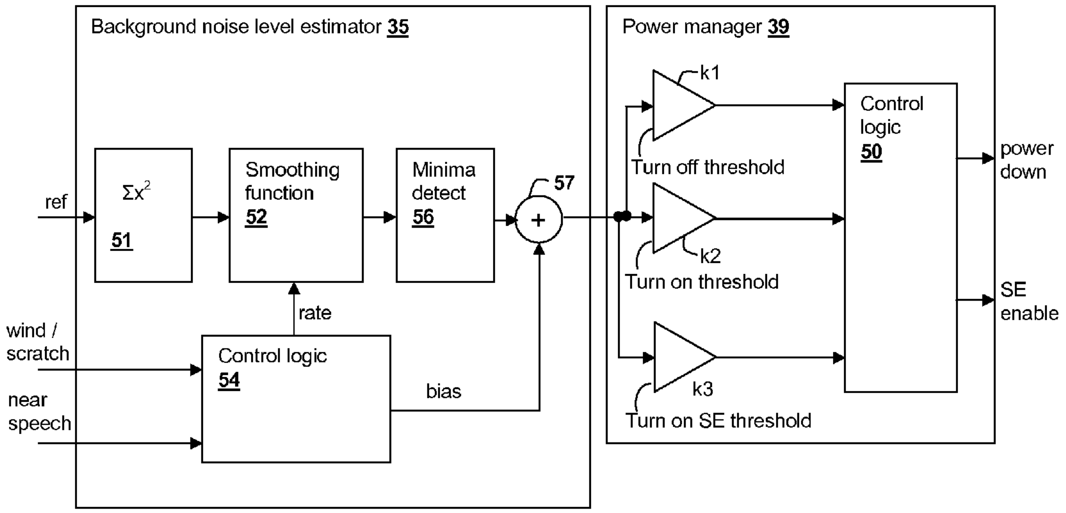
FIG. 4 is a block diagram depicting an example of details of exemplary background noise estimator 35 and power manager 39 within ANC circuit 30 of FIG. 3.

Referring now to FIG. 4, details of an exemplary background noise level estimator 35 and power manager 39 are shown, which detail an algorithm that is implemented within wireless telephone 10 to estimate background noise. Background noise level estimator 35 includes a noise power computation ($\Sigma x^2$) block 51 that computes a measure of the ongoing (instantaneous) noise power of reference microphone signal ref. The output of noise power computation block 51 provides an input to a smoothing function block 52, which in the example circuit applies an exponential smoothing to the noise power. The rate of the smoothing is controlled by control signal(s) rate provided by a control logic 54 that selects from different exponential smoothing coefficients applied by smoothing function block 52 according to indications wind/scratch and near speech, provided from wind/scratch detector 38 and near speech detector 37 of FIG. 3, respectively. A minima detection block 56 detects the minimum value of the smoothed instantaneous power of reference microphone signal ref over a predetermined time interval, which is programmable in order to control the criteria for eliminating non-stationary noise sources in reference microphone signal ref. The output of minima detection block 56 is biased by combiner 57 with a bias value selected by control logic 54 in accordance with the predetermined time interval and smoothing factors/rate being applied to the output of power computation block 51. The output of combiner 57 is used as an estimate of the background noise present in reference microphone signal ref, which is then provided to power manager 39. Power manager 39 compares the background noise estimate to turn-on threshold and a turn-off threshold, operations which are symbolized by comparators k2 and k1, respectively. A control logic 50 determines whether to de-assert indication power down if indication power down is asserted, according to whether the background noise exceeds the turn-on threshold, and whether to assert indication power down if indication power down is de-asserted, according to whether the background noise exceeds the turn-off threshold. The turn-on threshold is generally set to a value between 3 dB and 10 dB greater than the turn-off threshold, in order to provide a suitable amount of hysteresis for the power management of circuits within personal audio device that are power managed by indication power down. Another comparator k3 can be optionally provided to implement an intermediate level of power management of the ANC circuits. In the depicted example, a threshold value between the power up and power down threshold is used to inform control logic 50 that the background noise estimate is between the turn-on threshold and the turn-off threshold and above a "turn-on SE threshold" that causes control logic 50 to assert control signal SE enable, while maintaining control signal power down in the power down state. Table I below illustrates an exemplary set of power conservation modes.

TABLE I

| power down | SE enable | SE Circuits | W Circuits |
|---|---|---|---|
| 0 | 1 | Power-up/Enabled | Power-up/Enabled |
| 1 | 1 | Power-up/Enabled | Power-down/Disabled |
| 1 | 0 | Power-down/Disabled | Power-down/Disabled |

Figure 5:
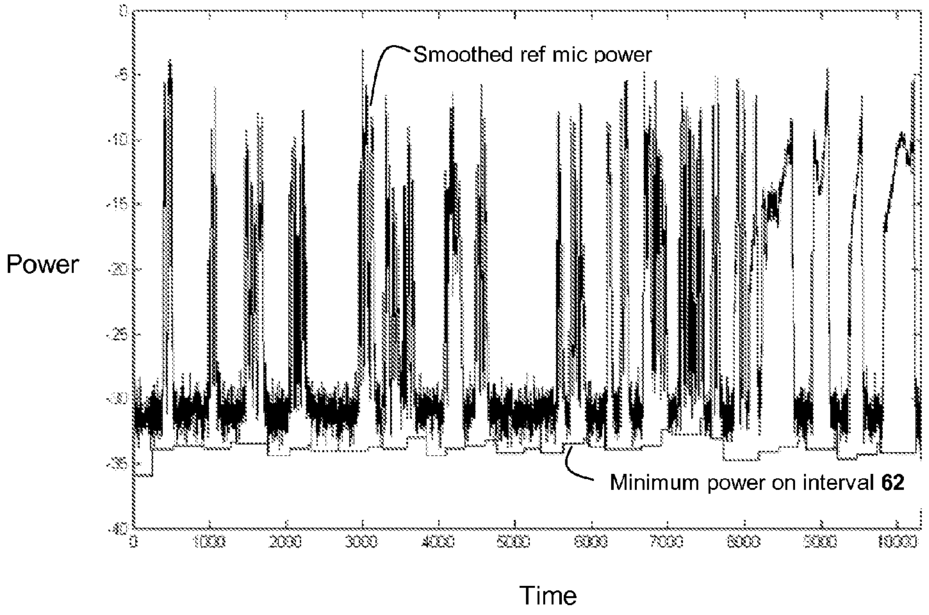
FIG. 5 is a signal waveform diagram illustrating operation of background noise estimator 35 of FIG. 4.

Referring now to FIG. 5, a waveform diagram illustrating the operation of background noise level estimator 35 is shown. A smoothed reference microphone power 60 is shown as a value that is rapidly changing over time with respect to the actual background noise power estimate, which is yielded by the value of a minimum power on each interval 62. The predetermined interval used to filter non-stationary sources of noise can be seen as the width of the smallest steps in waveform minimum power on interval 62, and as mentioned above, can be adjusted in order to control the criteria used to filter non-stationary noise source contributions from the background noise estimate.

Figure 6:
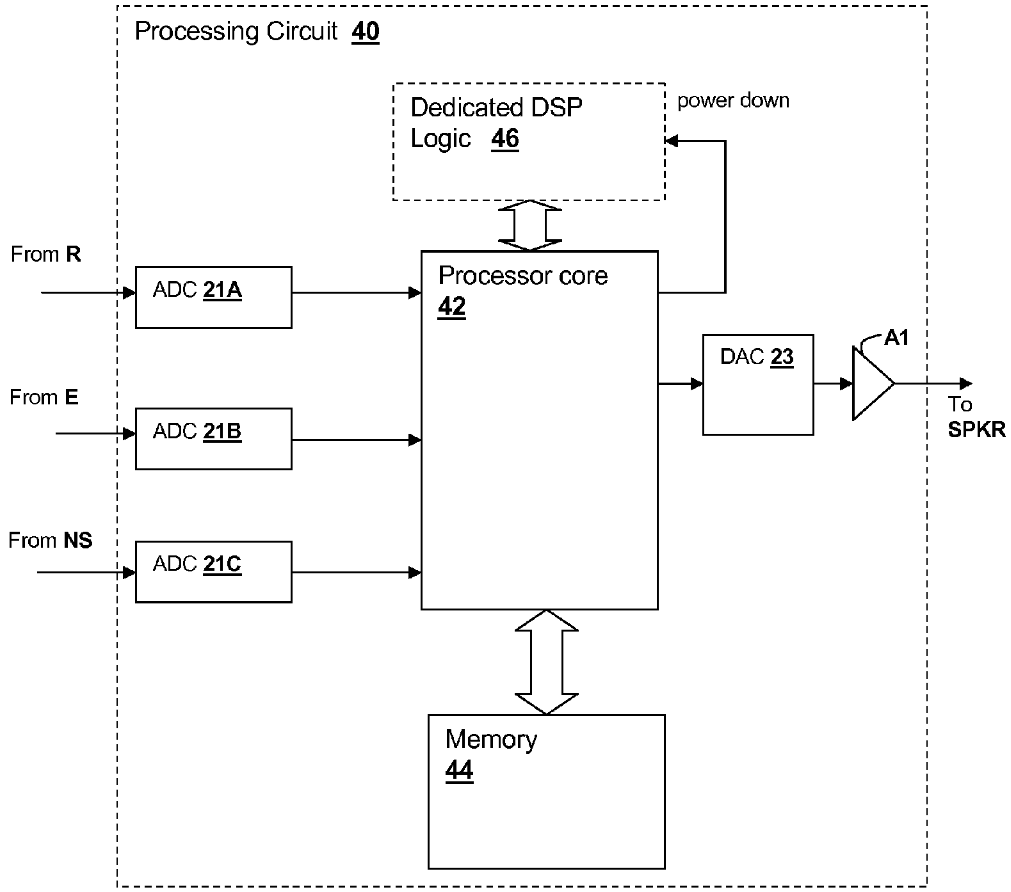
FIG. 6 is a block diagram depicting signal processing circuits and functional blocks within CODEC integrated circuit 20.

Referring now to FIG. 6, a block diagram of an ANC system is shown for implementing ANC techniques as depicted in FIG. 3, and having a processing circuit 40 as may be implemented within CODEC integrated circuit 20 of FIG. 2. Processing circuit 40 includes a processor core 42 coupled to a memory 44 in which are stored program instructions comprising a computer-program product that may implement some or all of the above-described ANC techniques, as well as other signal processing. Optionally, a dedicated digital signal processing (DSP) logic 46 may be provided to implement a portion of, or alternatively all of, the ANC signal processing provided by processing circuit 40. In the illustrated example processor core 42 provides control signal power down to DSP logic 46, so that the logic implementing filters or other DSP circuits can be shut down when ANC operation is not needed. Further, the state of control signal power down can alternatively, or in combination, be used to control the operation of processor core 42 so that power is conserved. For example, processor core 42 could be halted if the background noise level estimate and comparison is performed entirely in discrete circuits, or the program code executed by processor core 42 may periodically enter a sleep mode, intermittently resuming operation to measure the background noise level in order to update the state of control signal power down. Processing circuit 40 also includes ADCs 21A-21C, for receiving inputs from reference microphone R, error microphone E and near speech microphone NS, respectively. In alternative embodiments in which one or more of reference microphone R, error microphone E and near speech microphone NS have digital outputs, the corresponding ones of ADCs 21A-21C are omitted and the digital microphone signal(s) are interfaced directly to processing circuit 40. DAC 23 and amplifier A1 are also provided by processing circuit 40 for providing the speaker output signal, including anti-noise as described above. The speaker output signal may be a digital output signal for provision to a module that reproduces the digital output signal acoustically.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

at least one microphone mounted on the housing for providing at least one microphone signal indicative of the ambient audio sounds; and a processing circuit that generates the anti-noise signal using an adaptive filter to reduce the presence of the ambient audio sounds heard by the listener in conformity with the at least one microphone signal, and wherein the processing circuit further estimates a background noise level from the at least one microphone signal and sets a power conservation mode of the personal audio device in conformity with a magnitude of the estimated background noise level, wherein the processing circuit estimates the background noise level from a minimum value of noise sources within a time interval having a predetermined duration using a noise power measurement algorithm that measures the at least one microphone signal using a minima-tracking algorithm over the time interval to filter non-stationary noise sources and non-noise sources from the at least one microphone signal.

2. The personal audio device of claim 1, wherein the processing circuit further sets a full power mode of the personal audio device in response to detecting that the background noise level is greater than a predetermined threshold.

3. The personal audio device of claim 2, wherein the processing circuit further sets a lower-power operating mode of the personal audio device in response to detecting that the background noise level is less than a second value, wherein the second value is greater than the predetermined threshold by a difference in the range of 3 decibels to 10 decibels.

4. The personal audio device of claim 1, wherein the predetermined duration is adjustable to vary a property of the non-stationary noise sources filtered from the at least one microphone signal.

5. The personal audio device of claim 1, wherein the processing circuit filters the minimum value of the noise sources provided by the noise power measurement algorithm with a smoothing function to control a rate of change of the estimate of the background noise level used to detect whether or not to set the power conservation mode.

6. The personal audio device of claim 5, wherein the processing circuit implements a scratch or wind noise detection algorithm, and wherein the processing circuit adjusts the smoothing function to reduce the rate of change of the smoothing function in response to detecting scratch or wind noise, whereby the estimate of the background noise remains accurate in the presence of scratch or wind noise.

7. The personal audio device of claim 5, wherein the processing circuit implements a near speech detection algorithm, and wherein the processing circuit adjusts the smoothing function to reduce the rate of change of the smoothing function in response to detecting of near speech, whereby the estimate of the background noise remains accurate in the presence of near speech.

8. The personal audio device of claim 5, wherein the smoothing function is an exponential smoothing function.

9. The personal audio device of claim 1, wherein the processing circuit compares the background noise level to multiple thresholds and sets one of multiple power conservation modes of the personal audio device in response to a result of the comparisons.

10. A method of countering effects of ambient audio sounds by a personal audio device, the method comprising:

adaptively generating an anti-noise signal using an adaptive filter to reduce the presence of the ambient audio sounds heard by the listener in conformity with the at least one microphone signal;

combining the anti-noise signal with source audio;

providing a result of the combining to a transducer;

measuring the ambient audio sounds with at least one microphone;

estimating a background noise level from a minimum value of noise sources within a time interval having a predetermined duration by measuring the at least one microphone signal using a minima-tracking algorithm over the time interval to filter non-stationary noise sources and non-noise sources from the at least one microphone signal; and setting a power conservation mode of the personal audio device in conformity with a magnitude of the estimated background noise level.

11. The method of claim 10, wherein the setting a power conservation mode further comprises:

detecting that the background noise level is greater than a predetermined threshold; and setting a full power mode of the personal audio device in response to detecting that the background noise level is greater than the predetermined threshold.

12. The method of claim 11, wherein the setting a power conservation mode further sets a lower-power operating mode of the personal audio device in response to detecting that the background noise level is less than a second value, wherein the second value is greater than the predetermined threshold by a difference in the range of 3 decibels to 10 decibels.

13. The method of claim 10, wherein the estimating further comprises adjusting the predetermined duration to vary a property of the non-stationary noise sources filtered from the at least one microphone signal.

14. The method of claim 10, wherein the estimating further comprises filtering the minimum value of the noise sources provided by the noise power measurement algorithm with a smoothing function to control a rate of change of the estimate of the background noise level used to detect whether or not to set the power conservation mode.

15. The method of claim 14, further comprising:

detecting scratch or wind noise detection; and adjusting the smoothing function to reduce the rate of change of the smoothing function in response to the detecting scratch or wind noise, whereby the estimate of the background noise remains accurate in the presence of scratch or wind noise.

16. The method of claim 14, further comprising:

detecting near speech; and adjusting the smoothing function to reduce the rate of change of the smoothing function in response to detecting near speech, whereby the estimate of the background noise remains accurate in the presence of near speech.

17. The method of claim 14, wherein the smoothing function is an exponential smoothing function.

18. The method of claim 10, further comprising comparing the background noise level to multiple thresholds, and wherein the setting sets one of multiple power conservation modes of the personal audio device in response to a result of the comparing.

19. An integrated circuit for implementing at least a portion of a personal audio device, comprising:

an output for providing an output signal to an output transducer including both source audio for playback to a listener and an anti-noise signal for countering the effects of ambient audio sounds in an acoustic output of the transducer;

at least one microphone input for receiving at least one microphone signal indicative of the ambient audio sounds; and a processing circuit that adaptively generates the anti-noise signal using an adaptive filter to reduce the presence of the ambient audio sounds heard by the listener in conformity with the at least one microphone signal, and wherein the processing circuit further estimates a background noise level from the at least one microphone signal and sets a power conservation mode of the personal audio device in conformity with a magnitude of the estimated background noise level, wherein the processing circuit estimates the background noise level from a minimum value of noise sources within a time interval having a predetermined duration using a noise power measurement algorithm that measures the at least one microphone signal using a minima-tracking algorithm over the time interval to filter non-stationary noise sources and non-noise sources from the at least one microphone signal.

20. The integrated circuit of claim 19, wherein the the processing circuit further sets a full power mode of the personal audio device in response to detecting that the background noise level is greater than a predetermined threshold.

21. The integrated circuit of claim 20, wherein the processing circuit further sets a lower-power operating mode of the personal audio device in response to detecting that the background noise level is less than a second value, wherein the second value is greater than the predetermined threshold by a difference in the range of 3 decibels to 10 decibels.

22. The integrated circuit of claim 19, wherein the predetermined duration is adjustable to vary a property of the non-stationary noise sources filtered from the at least one microphone signal.

23. The integrated circuit of claim 19, wherein the processing circuit filters the minimum value of the noise sources provided by the noise power measurement algorithm with a smoothing function to control a rate of change of the estimate of the background noise level used to detect whether or not to set the power conservation mode.

24. The integrated circuit of claim 23, wherein the processing circuit implements a scratch or wind noise detection algorithm, and wherein the processing circuit adjusts the smoothing function to reduce the rate of change of the smoothing function in response to detecting scratch or wind noise, whereby the estimate of the background noise remains accurate in the presence of scratch or wind noise.

25. The integrated circuit of claim 23, wherein the processing circuit implements a near speech detection algorithm, and wherein the processing circuit adjusts the smoothing function to reduce the rate of change of the smoothing function in response to detecting of near speech, whereby the estimate of the background noise remains accurate in the presence of near speech.

26. The integrated circuit of claim 23, wherein the smoothing function is an exponential smoothing function.

27. The integrated circuit of claim 19, wherein the processing circuit compares the background noise level to multiple threshold and sets one of multiple power conservation modes of the personal audio device in response to a result of the comparisons.

* * * * *